United States Patent [19]

Miyashita et al.

[11] 4,263,294
[45] Apr. 21, 1981

[54] MAYTANSINOIDS, PHARMACEUTICAL COMPOSITIONS THEREOF AND METHOD OF USE THEREOF

[75] Inventors: Osamu Miyashita, Osaka; Hiroshi Akimoto, Nishinomiya, both of Japan

[73] Assignee: Takeda Chemical Industries, Ltd., Osaka, Japan

[21] Appl. No.: 93,742

[22] Filed: Nov. 13, 1979

[30] Foreign Application Priority Data

Nov. 20, 1978 [JP] Japan .................................. 53-143857
Jan. 22, 1979 [JP] Japan .................................... 54-6307

[51] Int. Cl.³ .................. A61K 31/535; C07D 498/16; C07D 521/00
[52] U.S. Cl. .......................... 424/248.54; 260/239.3 P
[58] Field of Search ................................. 260/239.3 P; 424/248.54

[56] References Cited

U.S. PATENT DOCUMENTS

| | | | |
|---|---|---|---|
| 3,896,111 | 7/1975 | Kupchan et al. | 260/239.3 T |
| 4,137,230 | 1/1979 | Hashimoto et al. | 260/239.3 P |
| 4,162,940 | 7/1979 | Higashide et al. | 260/239.3 P |

OTHER PUBLICATIONS

Kupchan et al., "J. Med. Chem.", (1978), vol. 21, No. 1, pp. 31–37.
Noller, "Chemistry of Organic Compounds," 2nd Ed., (1957), pp. 310 and 317.

*Primary Examiner*—Robert T. Bond

*Attorney, Agent, or Firm*—Wegner & Bretschneider

[57] ABSTRACT

Novel maytansinoids of the formula:

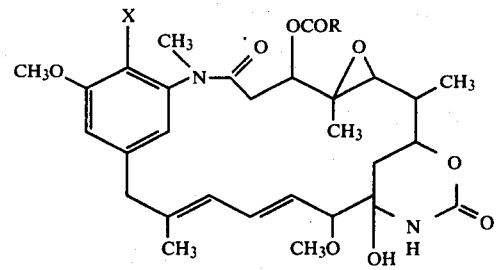

wherein X is H or Cl, and R is

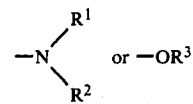

wherein $R^1$ and $R^2$ may be the same or different, and each is H or a substituted or unsubstituted hydrocarbon residue or heterocyclic group, or $R^1$ and $R^2$ may, taken together with the adjacent N atom, form a heterocyclic group, and $R^3$ is a substituted or unsubstituted hydrocarbon residue, have antimitotic, antitumor and antimicrobial activities.

9 Claims, No Drawings

MAYTANSINOIDS, PHARMACEUTICAL COMPOSITIONS THEREOF AND METHOD OF USE THEREOF

This invention relates to novel maytansinoid compounds of the formula:

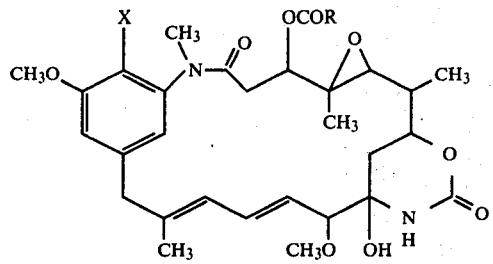

wherein X is H or Cl, and R is

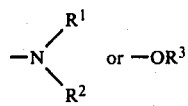

wherein $R^1$ and $R^2$ may be the same or different, and each is H or a substituted or unsubstituted hydrocarbon residue or heterocyclic group, or $R^1$ and $R^2$ may, taken together with the adjacent N atom, form a heterocyclic group, and $R^3$ is a substituted or unsubstituted hydrocarbon residue, and to methods for production and use of the compounds (I).

Referring to the above formula (I) wherein R is

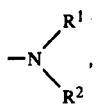

the hydrocarbon residues designated by $R^1$ and $R^2$ may for example be, hydrocarbon residues up to 18 carbon atoms. Said hydrocarbon residues include alkyl, alkenyl, cycloalkyl, cycloalkenyl, cycloalkylalkyl, cycloalkenylalkyl, aryl, aralkyl, phenylcycloalkyl, cycloalkylphenyl and biphenyl.

As examples of said alkyl group, there may be mentioned alkyl groups of about 1 to 18 carbon atoms (e.g. methyl, ethyl, propyl, isopropyl, butyl, isobutyl, sec-butyl, tert-butyl, pentyl, isopentyl, hexyl, isohexyl, heptyl, octyl, nonyl, decyl, undecyl, dodecyl, tetradecyl, hexadecyl, octadecyl, 1,2-dimethylpropyl, 1-ethylpropyl, 1,2,2-trimethylpropyl, 1-propylbutyl, 2-ethylhexyl). As examples of said alkenyl group, there may be mentioned alkenyl groups of about 1 to 18 carbon atoms (e.g. vinyl, allyl, 1,3-pentadienyl, oleyl).

As examples of said cycloalkyl group, there may be mentioned cycloalkyl groups of about 3 to 10 carbon atoms (e.g. cyclopropyl, cyclobutyl, cyclopentyl, cyclohexyl, cycloheptyl, cyclooctyl, norbonyl, adamantyl), each of which may be fused to a benzene ring (e.g. 1- or 2-indanyl, benzocyclobutyl etc.) As example of said cycloalkenyl group, there may be mentioned cycloalkenyl groups of about 3 to 10 carbon atoms (e.g. 1-cyclobutenyl, 1-, 2- or 3-cyclopentenyl, 1-, 2- or 3-cyclohexenyl, 4-cycloheptenyl, 4-cyclooctenyl, 1,4-cyclohexadienyl, 4-norbornenyl, 2,4,6-cycloheptatrienyl).

As examples of said cycloalkylalkyl and cycloalkenylalkyl groups, there may be mentioned $C_{3-10}$ cycloalkyl-$C_{1-6}$ alkyl or $C_{3-10}$ cycloalkenyl-$C_{1-6}$ alkyl groups. Such cycloalkyl groups may include cyclopropylmethyl, cyclobutylethyl, cyclopentylmethyl, cyclopentylethyl, cyclohexylmethyl, cyclohexylethyl, cyclohexylpropyl, α-methylcyclohexylpropyl, 1-adamantylmethyl, etc. and such cycloalkenylalkyl groups may include 1-, 2- or 3-cyclopentenylmethyl, 1-, 2- or 3-cyclohexenylmethyl, 4-cycloheptenylpropyl, 1,4-cyclohexadienylmethyl, etc.

As examples of said aryl group, there may be mentioned phenyl, α- or β-naphthyl, etc.

The aralkyl group includes aryl-$C_{1-6}$ alkyl, preferably phenyl-$C_{1-6}$ alkyl such as benzyl, phenethyl, 3-phenylpropyl, α-methylbenzyl, 1-methyl-3-phenylpropyl, 4-phenylbutyl, etc.

The phenylcycloalkyl group includes phenyl-$C_{3-10}$ cycloalkyl, especially phenyl $C_{3-7}$ cycloalkyl such as 2-phenylcyclopropyl, 4-phenylcyclohexyl, etc. The cycloalkylphenyl group includes $C_{3-10}$ (especially $C_{3-7}$) cycloalkylphenyl such as 4-cyclopentylphenyl, 4-cyclohexylphenyl, etc. As examples of said biphenyl group, there may be mentioned 4-biphenyl and so forth.

The heterocyclic groups designated by $R^1$ and $R^2$ include saturated or unsaturated 4-, 5- or 6-membered heterocyclic groups including N, O or/and S atoms, and a benzene ring may optionally be fused to such heterocyclic groups. Thus, there may be mentioned azetidinyl, pyrrolyl, furyl, thienyl, thiazolyl, isothiazolyl, oxazolyl, isoxazolyl, pyrazolyl, imidazolyl, pyridyl, pyrimidinyl, pyrazinyl, triazinyl, quinolyl, quinazolyl, quinoxalyl, indolyl, benzofuranyl, benzothienyl, etc.

$R^1$ and $R^2$ may, taken together with the adjacent N atom, form a heterocyclic group. Such heterocyclic groups include 4-, 5- or 6-membered heterocyclic groups containing N atom (e.g. azetidinyl, pyrrolidinyl, piperazinyl, morpholinyl, etc.).

The hydrocarbon residues and heterocyclic groups $R^1$ and $R^2$ and the heterocyclic group

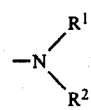

may optionally be substituted. The substituents include, for example, alkoxy groups of 1 to 4 carbon atoms (e.g. methoxy, ethoxy, propoxy, isopropoxy, butoxy, isobutoxy, sec-butoxy), alkylthio groups of 1 to 4 carbon atoms (e.g. methylthio, ethylthio, propylthio, isopropylthio, butylthio), phenoxy, phenylthio, cyclohexyloxy, halogen (e.g. fluorine, chlorine, bromine, iodine), cyano, $C_{2-5}$ alkoxycarbonyl groups (e.g. methoxycarbonyl, ethoxycarbonyl, propoxycarbonyl, isopropoxycarbonyl, butoxycarbonyl, isobutoxycarbonyl, sec-butoxycarbonyl), benzyloxycarbonyl, nitro, aminosulfonyl and dialkylamino groups (e.g. dimethylamino, diethylamino, diisopropylamino, dibutylamino). One to 3 of such substituents may be present, and may be the same or different.

Substituents on the above-illustrated hydrocarbon residues other than alkyl and alkenyl groups, namely the hydrocarbon residues having cyclic moieties and the heterocyclic groups, may include, in addition to the substituents mentioned just above, alkyl groups (which may have the substituents mentioned for hydrocarbon residues $R^1$ and $R^2$) of about 1 to 4 carbon atoms (e.g. methyl, ethyl, propyl, isopropyl, butyl, trifluoromethyl, chloromethyl, 2-cyanoethyl, methoxymethyl, ethoxycarbonylmethyl, dimethylaminomethyl, etc.). The substituents on alkyls $R^1$ and $R^2$ include not only the groups mentioned as substituents on said hydrocarbon residue but also heterocyclic groups similar to those represented by $R^1$ and $R^2$ (which may be heterocyclic groups having further substituent(s).

As examples of substituted hydrocarbon residues $R^1$ and $R^2$, there may be mentioned 2-methoxyethyl, 3-methoxypropyl, β-methoxyisopropyl, 3-isopropoxypropyl, 3-sec-butoxypropyl, 3-cyclohexyloxypropyl, 3-phenoxypropyl, 2-chloroethyl, 3-chloropropyl, 4-chlorobutyl, 2-propylthioethyl, 2-phenylthioethyl 2-cyanoethyl, 5-cyanopentyl, 4-cyanocyclohexylmethyl, methoxycarbonylmethyl, ethoxycarbonylmethyl, 1- or 2-methoxycarbonylethyl, 1-methoxycarbonylisobutyl, 5-methoxycarbonylpentyl, dimethylaminopentyl, trifluoromethyl, 2-, 3- or 4-tolyl, xylyl, 2,4,5- or 2,4,6-trimethylphenyl, 2-, 3- or 4-chlorophenyl, 2,5-dichlorophenyl, 2-, 3- or 4-fluorophenyl, 4-bromophenyl, 4-iodophenyl, 2- or 3-trifluorophenyl, 2-, 3- or 4-nitrophenyl, 4-chloro-3-trifluoromethylphenyl, 2-methyl-4-nitrophenyl, 5-nitro-1-naphthyl, 8-chloro-1-naphthyl, 4-methoxycarbonylphenyl, 4-ethoxycarbonylphenyl, 4-aminosulfonylphenyl, 2-, 3- or 4-methoxyphenyl, 4-ethoxyphenyl, 2,5-dimethoxyphenyl, 1-methoxycarbonyl-2-phenethyl, 1-methoxycarbonyl-1-phenylmethyl, 2-, 3- or 4-methylbenzyl, 2-, 3- or 4-chlorobenzyl, 2- or 3-fluorobenzyl, 3-iodobenzyl, 2,4- or 3,4-dichlorobenzyl, 4-methoxybenzyl, α-methylbenzyl, 1,1-dimethylphenethyl, 4-methoxyphenethyl, 2-, 3- or 4-picolyl, 5-methyl-2-thenyl, 5-methylfurfuryl, 3-piperazinopropyl, 2-morpholinoethyl, 4-methyl-1-piperazinylpropyl, 2-(1-methyl-2-pyrrolidinyl)ethyl, 2-thiazolylmethyl, 2-methyl-4-oxazolylmethyl, 5-chloro-1-methyl-3-indolylethyl, etc.

As examples of substituted or unsubstituted heterocyclic groups $R^1$ and $R^2$, there may be mentioned 1-methyl-2-azetidinyl, 1-methyl-2-pyrrolyl, 5-methyl-2-furyl, 5-nitro-2-furyl, 3-methyl-2-thienyl, 4,5-dichloro-2-thienyl, 2-methyl-4-thiazolyl, 1-methyl-4-imidazolyl, 2-dimethyl-4-chloro-5-imidazolyl, 3,5-bis-methylthio-4-isothiazolyl, 3-methyl-5-isoxazolyl, 2-methyl-4-oxazolyl, 1-methyl-3-pyrazolyl, 2-, 3- or 4-pyridyl, 4,5,6-trichloro-2-pyrimidyl, 3,5,6-trichloro-2-pyrazinyl, 4,6-dichloro-2-s-triazinyl, 3- or 4-quinolyl, 2-quinazolyl, 2-quinoxalyl, 5-fluoro-1-methyl-3-indolyl, 2-benzofuryl, 2-benzothienyl, etc. when the heterocyclic group

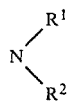

is substituted, it may for example represent 2-, 3- or 4-methyl-1-piperidinyl, 4-methyl-1-piperazinyl, 2,6-dimethylmorpholino, 2-propyl-1-piperidinyl, etc.

The group

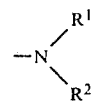

in which both $R^1$ and $R^2$ are members other than H includes, among others, dimethylamino, diethylamino, dipropylamino, diisopropylamino, diisobutylamino, dibenzylamino, diphenethylamino, diphenylpropylamino, N-methyl-N-benzylamino, N-ethyl-N-butylamino, N-methyl-N-cyclopentylamino, N-methyl-N-cyclohexylamino, N-methyl-N-furfurylamino, etc.

Referring to the above formula (I) wherein R is $-OR^3$, as examples of the hydrocarbon residue designated by $R^3$, there may be mentioned $C_{1-18}$ hydrocarbon residue such as alkyl, cycloalkyl, aryl or aralkyl.

As examples of said alkyl group, there may be mentioned alkyl groups of about 1 to 18 carbon atoms (e.g. methyl, ethyl, propyl, isopropyl, butyl, isobutyl, sec-butyl, tert-butyl, pentyl, hexyl, heptyl, octyl, nonyl, decyl, undecyl, dodecyl, tetradecyl, hexadecyl, octadecyl, 1-ethylpropyl, neopentyl, 1-ethylpentyl, 1- or 2-ethylhexyl). Preferably, it is an alkyl group of about 1 to 8 carbon atoms.

As examples of said cycloalkyl, there may be mentioned cycloalkyl groups of about 3 to 10 carbon atoms (e.g. cyclopropyl, cyclobutyl, cyclopentyl, cyclohexyl, cycloheptyl, cyclooctyl, adamantyl).

As examples of said aryl group, there may be mentioned phenyl, α- or β-naphthyl, etc.

The aralkyl group includes, for example, an alkyl group of about 1 to 4 carbon atoms substituted by an aryl group as mentioned above, especially by phenyl. As examples of said aralkyl group, there may be mentioned benzyl, phenethyl, 1- or 3-phenylpropyl, 1-phenylethyl, 1-methyl-3-phenylpropyl, 4-phenylbutyl, etc.

The above-mentioned hydrocarbon residue may be substituted by such groups as alkoxy groups of 1 to 4 carbon atoms (e.g. methoxy, ethoxy, propoxy, isopropoxy, butoxy, isobutoxy, sec-butoxy), phenoxy, benzyloxy, halogen (e.g. fluorine, chlorine, bromine, iodine), cyano and so forth. One to 3 of such substituents may be present, and may be the same or different.

The substituent or substituents on the above-illustrated hydrocarbon residues $R^3$ other than alkyl groups, namely cycloalkyl, aryl, aralkyl and other cyclic groups, include, in addition to those substituents mentioned above, alkyl groups of 1 to 4 carbon atoms (e.g. methyl, ethyl, propyl, isopropyl, butyl), halogenated alkyl groups of 1 to 4 carbon atoms (e.g. chloromethyl, bromomethyl, dichloromethyl, chlorodifluoromethyl, trifluoromethyl), etc.

As examples of the substituted alkyl designated by $R^3$, there may be mentioned 2-methoxyethyl, 2-ethoxyethyl, 2-butoxyethyl, 4-ethoxybutyl, chloromethyl, 1- or 2-chloroethyl, 2-bromoethyl, 2-fluoroethyl, 3-chloropropyl, 2,3-dichloropropyl, 2-chloroisopropyl, 1-chloromethyl-2-chloroethyl, 2,2,2-trichloroethyl, 2,2,2-trifluoroethyl, 1- or 2-cyanopropyl, etc. As examples of the substituted cycloalkyl $R^3$, there may be mentioned 1-methylcyclobutyl, 1-methylcyclopentyl, 1-methylcyclohexyl, etc. As examples of the substituted aralkyl $R^3$, there may be mentioned 2-, 3- or 4-chlorobenzyl, 4-bromobenzyl, 4-methoxybenzyl, 2,5- or 3,4-dimethoxybenzyl, 3-chloro-4-methylbenzyl, etc. As examples of the substituted aryl R³, there may be mentioned 2-, 3- or 4-methylphenyl, 2-, 3- or 4-methoxyphenyl, 4-ethoxyphenyl, 2-, 3- or 4-chlorophenyl, 4-fluorophenyl, 2,4-dichlorophenyl, 2-, 3- or 4-chloromethylphenyl, 4-trifluoromethylphenyl, 4-bromophenyl, 3-dimethylaminophenyl, etc.

In the maytansinoid compounds of the present invention, desirable are compounds of formula (I) wherein R is

wherein R¹ and R² may be the same or different, and each is H, $C_{1-18}$ alkyl, $C_{1-18}$ alkenyl, $C_{3-10}$ cycloalkyl to which a benzene ring may be fused, $C_{3-10}$ cycloalkenyl, $C_{3-10}$ cycloalkyl-$C_{1-6}$ alkyl, $C_{3-10}$ cycloalkenyl-$C_{1-6}$ alkyl, phenyl, naphthyl, phenyl-$C_{1-6}$ alkyl, phenyl-$C_{3-10}$ cycloalkyl, $C_{3-10}$cycloalkylphenyl, biphenyl, or 4-, 5- or 6-membered heterocyclic group containing N, O or-/and S which may have a fused benzene ring, said hydrocarbon residues and heterocyclic group being unsubstituted or substituted by $C_{1-4}$ alkyl, $C_{1-4}$ alkoxy, $C_{1-4}$ alkylthio, phenoxy, phenylthio, cyclohexyloxy, halogen, cyano, carboxyl, $C_{2-5}$ alkoxycarbonyl, benzyloxycarbonyl, nitro, aminosulfonyl or di-$C_{1-4}$ alkylamino; or R¹ and R² may, taken together with the adjacent N atom, form 4-, 5- or 6-membered heterocyclic group containing N atom, or desirable are compounds of formula (I) wherein R is —OR³ wherein R³ is $C_{1-18}$ alkyl, $C_{3-10}$ cycloalkyl, phenyl, naphthyl or phenyl-$C_{1-4}$ alkyl, said hydrocarbon residues being unsubstituted or substituted by $C_{1-4}$ alkyl, halogenated $C_{1-4}$ alkyl, $C_{1-4}$ alkoxy, phenoxy, benzyloxy, halogen or cyano.

In the maytansinoid compounds of the present invention, more desirable are compounds of formula (I) wherein R is

wherein
R¹ and R² may be the same or different, and each is H, $C_{1-18}$ alkyl, $C_{3-7}$ cycloalkyl, phenyl, naphthyl or pyridyl, said alkyl, cycloalkyl, phenyl, naphthyl and pyridyl being unsubstituted or substituted by $C_{1-4}$ alkyl, $C_{1-4}$ alkoxy, carboxyl, $C_{2-5}$ alkoxycarbonyl or di-$C_{1-4}$ alkylamino, or compounds of formula (I) wherein R is —OR³ wherein R³ is $C_{1-8}$ alkyl, phenyl or phenyl-$C_{1-4}$ alkyl.

The maytansinoid compound (I) according to this invention can be produced, for example by reacting maytansinol or dechloromaytansinol of the formula:

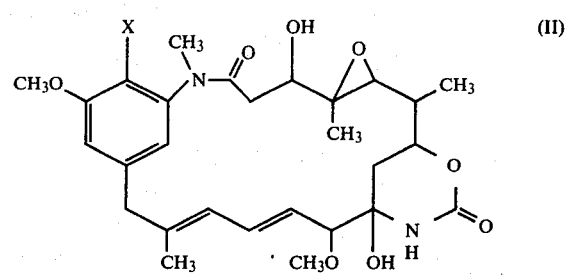

wherein X has the same meaning as defined above, with a compound of the formula:

ZCOR (III)

wherein Z is halogen and R is as defined above, in the presence of a base.

Referring to the above formula (III), the halogen atom Z may for example be Cl and Br.

This reaction is normally conducted in a solvent. The solvent includes, for example, ethers (e.g. dimethyl ether, diethyl ether, dioxane, tetrahydrofuran), hydrocarbons (e.g. petroleum ether, hexane, benzene, toluene, xylene) and suitable mixtures of such solvents, tetrahydrofuran being especially desirable.

The base for use in this reaction includes, for example, alkali metals (e.g. lithium, sodium), alkali metal hydrides (e.g. sodium hydride), organometallic compounds of alkali metals [e.g. butyllithium, sec-butyllithium, tert-butyllithium, sodium naphthalene, dimcylsodium ($CH_3SOCH_2Na$)], phenyl magnesium bromide, etc. The amount of such base, relative to starting compound (II), is normally in the range of about 3 to 20 molar equivalents and preferably about 4 to 10 molar equivalents.

The compound (III) may be used, relative to starting compound (II), in a proportion of about 3 to 20 molar equivalents, preferably about 5 to 10 molar equivalents.

The sequence of reactions etc. is not particularly critical. However, it is generally advantageous to first dissolve compound (II) in solvent, then add a solution of the base thereto and finally add compound (III). The reaction is normally carried out at a temperature of about $-78°$ C. to $+50°$ C. and, preferably, about $-30°$ C. to $+40°$ C.

It should be understood that this reaction may be carried out, in certain cases, by employing a reactive derivative of the compound (III) other than the halide mentioned hereinbefore.

As a different procedure of carbamoylation reaction, there is a process in which maytansinol or dechloramaytansinol of the formula (II) is reacted with a compound of the formula:

R¹'—N=C=O (IV)

wherein R¹' has the same meaning as that of R¹ except that R¹ and R² form a heterocyclic group. Thus, R¹' in the above (IV) means H or the substituted or unsubstituted hydrocarbon residue or heterocyclic group as defined hereinbefore for R¹. This reaction yields a maytansinoid compound having H as R² in the formula (I).

This reaction is preferably conducted in solution. The solvent used for this reaction is not particularly critical as to its type but it is only necessary that the solvent has no active hydrogen atom which would react with compound (IV) (said active hydrogen may for example be that of —OH or —NH—). As examples of such solvents, there may be mentioned the same solvents as mentioned hereinbefore. The reaction is preferably carried out in an anhydrous solvent of the above mentioned type.

The compound (IV) may theoretically be used in an equimolar proportion relative to compound (II) but in view of its possible loss by water in the solvent or by a dimerization reaction of compound (IV) itself, as it is the case when (IV) is an activated one, it is desirable to employ the compound (IV) in slight excess. The compound (IV) is, therefore, desirably employed in a proportion of 2 to 20 equivalents and, preferably, about 2 to 5 equivalents. The reaction may be conducted in the temperature range of −20° C. to +80° C., preferably 5° C. to 40° C. In case the compound (IV) is an active compound (usually, when nitro- or polyhalosubstituted), the two reactants may be simply admixed. Generally, however, use of a catalyst is advantageous. The catalyst for use includes basic substances normally used for the carbamoylation of alcohols or phenols with an isocyanate ester. Thus, there may be mentioned tertiary amines (e.g. triethylamine, pyridine), alkali metal alkoxides (e.g. potassium-tert-butoxide, sodium methoxide), alkali- metal acetates (e.g. lithium-, sodium-, potassium-, rubidium- and cesium acetates) and metal salts (e.g. chlorides of lead, bismuth, tin, cobalt, zinc, cadmium, manganese, titanium, iron, copper, etc., and organic carbonate salts, etc.), metal complex or organic metal compound (e.g. 2, 4-pentadiene-metal complexes, ferrocenes, dibutyltin oxide, dioctylin oxide, dibutyltin - bis-laurate, etc.). Among these catalysts, anhydrous zinc chloride is especially suitable for the contemplated reaction from the standpoint of selectivity and reaction rate. The catalyst may be used in catalytic amounts and may usually range from about 0.01 to 10 molar equivalents, preferably from about 0.1 to 3 molar equivalents.

When, as said catalyst, cuprous chloride is employed, the compound of the following formula (V) may be obtained in certain instances.

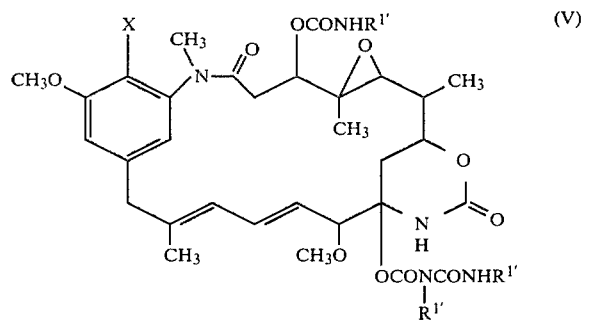

(V)

[wherein X and $R^{1'}$ have the same meanings as defined above]

This compound (V) can be easily converted to the desired compound (I) wherein $R^2$ is H, by treatment with an acid. As examples of said acid, there may be mentioned mineral acids (e.g. hydrogen chloride, hydrochloric acid, sulfuric acid, phosphoric acid, etc.) and strong organic acids (e.g. benzenesulfonic acid, toluenesulfonic acid, methanesulfonic acid, trifluoroacetic acid, trichloroacetic acid, etc.) or the like preferably, trifluoroacetic acid is employed. The reaction is desirably carried out in solution. The solvent for this reaction may be one of those mentioned hereinbefore in connection with the carbamoylation reaction with compound (IV). This reaction normally proceeds fast at a temperature from about −20° C. to +40° C. There are cases in which this reaction may be accomplished simply by passing a crude carbamoylation product including (V) through a column of silica gel.

The compound (I) produced by the above-mentioned methods may be converted to another compound (I) by a per se conventional procedure (e.g. hydrolysis, alkylation, esterification, quaternization).

The maytansinoid compound (I) thus produced can be easily isolated by subjecting the reaction mixture to a conventional purification procedure such as concentration, solvent extraction, chromatography, recrystallization, etc. When compound (I) has been produced as a mixture of isomers (e.g. D- and L-isomers), it can be resolved or separated into the component isomers by a per se conventional procedure, e.g. silica gel chromatography. The maytansinoid compound (I) of this invention encompasses those isomers and their mixtures.

The maytansinoid compound (I) according to this invention has strong antimitotic and antitumor activities with comparatively low toxicity and therefore can be orally or parenterally administered to tumor-bearing warm blooded animals (e.g. mouse, rat, rabbit, dog, cat, human being) for prolongation of their survival times. The compound (I) is normally administered in the form of a suitable pharmaceutical preparation (e.g. injectable preparation) as formulated with a conventional carrier, diluent or the like.

When compound (I) is administered in the form of an injectable preparation, it may be given subcutaneously, intraperitoneally, intravenously or intramuscularly, for instance. The dosage of compound (I) varies with the kind, symptom, administration route, etc. but, for example, in case of intravenous administration for prolonging life span of the animal suffering from leukemia or melanoma, it may be decided from the range of about 1 to 1000 µg/kg body weight per dose, preferably about 20 to 700 µg/kg body weight when compound (I) wherein R is

is employed, and preferably about 10 to 500 µg/kg body weight when compound (I) wherein R is —$OR^3$ is employed.

The injectable preparation can be prepared by the established pharmaceutical procedure; for example by dissolving about 50 µg to 3 mg of compound (I) in each about 0.5 ml of alcohol (e.g. ethanol), followed by addition of a sufficient amount of physiological saline to make a total of 10 ml. When a small dosage is indicated, the above solution may be further diluted with physiological saline.

The maytansinoid compounds (I) according to this invention are of value also in that they have antimicrobial activity, e.g. antifungal and antiprotozoal properties. Thus, for example, the maytansinoid compounds (I) are useful for treating *Tetrahymena pyriformis* W. As an antifungal or antiprotozoal agent, compound (I) is instrumental in assays of the bacterial flora of soil, active sludge, animal body fluids, etc. Thus, in such applications as the isolation of useful bacteria from soil samples and the activity assay of bacteria other than protozoa and fungi in the operation and analysis of active sludge systems for waste water treatment, and compound (I) specifically allows the bacteria to grow without permitting growth of fungi and protozoa which may also be present in the specimens. A typical such procedure may comprise adding a test specimen to a liquid or solid medium, then adding 0.1 ml of about 10 to 100 μg/ml of compound (I) in water with 1% methanol added and incubating the mixture.

The maytansinoid compound (I), at the dose level of 0.02 ml as a 1 mg/ml aqueous solution, inhibits growth of the causative microorganisms of stem rot, Helminthosporium leaf spot and sheath blight in rice plants and, therefore, can be used in the control of such plant diseases by spraying rice plants with a solution of compound (I) in 1% methanolwater, the concentration of which may range from about 0.5 to 5 μg/ml.

Maytansinol, the starting compound (II) for use in the production of the compounds according to this invention, is a known compound and a plant principle [Kupchan et al., J. Amer. Chem. Soc., 97, 5294 (1975)]. It can also be produced by reductive cleavage of maytansine and its analogs.

Maytansinol and dechloromaytansinol can also be produced advantageously by growing an Antibiotic C-15003-producing strain of the genus Nocardia (FERM-P No. 3992, IFO-13726, ATCC-31281) in a culture medium to obtain ansamitocin of formula (VI):

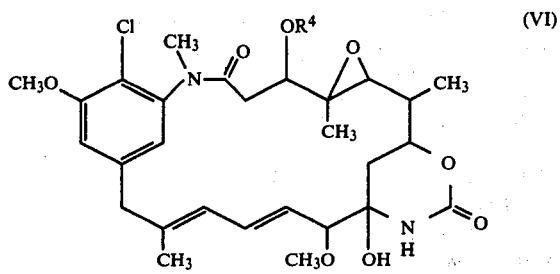

wherein $R^4$ is acetyl, propionyl, iso-butyryl, n-butyryl or iso-valeryl,
and reducing (VI) with a metal hydride such as $LiAlH_4$. [E. Higashide et al, Nature, Vol. 270, 721 (1977); U.S. Pat. No. 4,162,940 (Ser. No. 811,448)]

The starting compounds (III) and (IV) can be produced, for example, by the conventional procedures described in the following references (1) to (3), or by the application of such procedures to the corresponding starting compounds (e.g. amine, carboxylic acid, halide, etc.).

(1) W. Siefken, Ann. Chemie, 562, 79(1949).
(2) The Chemistry of Cyanates and Their Thio Derivatives, Part 2, Edited by S. Patai, John Wiley & Sons, 1977, Chapter 17, pages 619–654.
(3) K. Ninomiya, T. Shioiri and S. Yamada, Chem. Pharm. Bull 22, 1398(1974)

The following examples are intended to describe this invention in further detail and not to limit its scope.

REFERENCE EXAMPLE 1

In 800 ml of dry tetrahydrofuran (THF) is dissolved 15.0 g of antibiotic Ansamitocin mixture (12% of ansamitocin P-2, 71% of P-3 and 17% of P-4) and under dry nitrogen gas streams, the solution is cooled to $-50°$ C. in a dry ice-acetone bath. Then, 13.0 g of lithium aluminum hydride (LAH) is added in a single dose and the mixture is stirred at $-50°$ C. to $-22°$ C. for 2 hours. Then, at $-28°$ C., a further 3 g of LAH is added and the reaction mixture is stirred at $-28°$ C. to $-22°$ C. for 80 minutes. Thereafter, at $-50°$ C., 750 ml of 2 N HCl is added dropwise with caution and the reaction mixture is extracted three times with 2.6 l, 1.6 l and 0.8 l portions of ethyl acetate. The extracts are pooled, washed with a saturated aqueous solution of sodium chloride (100 ml×2) and dried ($MgSO_4$, 250 g). The solvent is distilled off under reduced pressure and the residue (13.6 g) is chromatographed on a column of silica gel (1.2 kg), elution being carried out with ethyl acetate-water (98.5: 1.5, V/V). The eluate is collected in 400-gram fractions. Fractions 35 through 52 are pooled, the solvent distilled off and the residue dried in vacuo to obtain 7.25 g of maytansinol. Then, fractions 53 through 68 are similarly treated to obtain 1.55 g of a substantially equimolar mixture of maytansinol and dechloromaytansinol. Similarly, fractions 69 through 86 yield 0.78 g of dechloromaytansinol.

This product is reprecipitated from chloroform-hexane to obtain 0.71 g of dechloromaytansinol.

m.p. 174°–179° C. (decompn.)

NMR spectrum ($CDCl_3$) δ ppm: 0.86(3H, s), 1.27(3H, d, J=ca. 6 Hz), 1.65(3H, s), 2.63(1H, d, J=9 Hz), 9.07(1H, d, J=13 Hz), 3.23(3H, s), 3.35(3H, s), 3.42(1H, d, J=13 Hz), 3.75(1H, d, J=9 Hz), 3.81(3H, s), 4.37(1H, m), 5.51(1H, dd, J=9 Hz & 15 Hz), 6.10(1H, d, J=11 Hz), 6.41(1H, dd, J=11 Hz & 15 Hz), 6.56(1H, d, J=2 Hz), 6.60(1H, s), 6.70(1H, approx. s), 6.97(1H, approx. s), Mass spectrum (m/e): 469, etc.

UV spectrum ($\lambda_{max}^{MeOH}$) nm: 231.5, 241.5, 250.5, 277.5, 286.

REFERENCE EXAMPLE 2

Production of 2-methoxycarbonylethyl isocyanate.

In 600 ml of dry toluene is dissolved 26.4 g of monomethyl succinate and to this, 55 g of diphenylphosphoryl azide and 22 g of triethylamine are added. The mixture is stirred for 3 hours at room temperature and, then, washed with ice-water and dried ($Na_2SO_4$). After filtration, the filtrate is concentrated to about one-third of its initial volume and, finally, is refluxed for 2 hours. Then, the solvent is distilled off, and the residue is subjected to distillation under reduced pressure to obtain 13.6 g of the above-indicated compound b.p.$_8$: 64°–66° C.

REFERENCE EXAMPLE 3

Production of 5-dimethylaminopentyl isocyanate.

In 136 ml of ethanol are dissolved 23.5 g of methyl 6-N, N-dimethylaminocaproate and 10.2 g of hydrazine hydrate, and the solution is refluxed overnight. An excess of oxalic acid-ethanol solution is added and the white precipitate is recovered by filtration. This precipitate is extracted with 300 ml of hot 50% aqueous ethanol. After cooling, the insolubles are filtered off and the filtrate evaporated to dryness to obtain 23.3 g of white crystals. The entire amount of the crystals are suspended in 136 ml of water and treated with 12.3 g of sodium nitrite under cooling. The reaction mixture is adjusted to pH 10.5 with 5 N-sodium hydroxide and extracted three times with 150 ml portions of benzene. The benzene layers are combined, washed with water and dried. This is refluxed for 1 hour and allowed to stand.

The solvent is distilled off with caution and the residue is further distilled under reduced pressure to 6.1 g of the desired compound. b.p.$_{14}$: 110°–115° C.

EXAMPLE 1

In 10 ml of dry dichloromethane is dissolved 56 mg of maytansinol (0.099 mmol), followed by addition of 24 mg. (0.202 mmol) of phenyl isocyanate. Then, 30 mg (0.221 mmol) of anhydrous zinc chloride is further added at room temperature (18°–23° C.). Thereafter, the mixture is stirred for 3 hours at the same temperature. The reaction mixture is washed with water, dried (Na$_2$SO$_4$) and concentrated. The residue is chromatographed on a column of silica gel [solvent: ethyl acetate/H$_2$O-saturated ethyl acetate=4:1, (V/V) to 3:1, (V/V)], the eluate being collected in 17-gram fractions. Fractions 9 through 17 are pooled, and the solvent is removed to obtain 58 mg of maytansinol 3-N-phenylcarbamate.

m.p.: 187°–189° C. (recrys. from ethyl acetate-hexane)

NMR spectrum (CDCl$_3$) δ ppm: 0.86(3H, s), 1.25(3H, d, J=4 Hz), 1.68(3H, s), 2.22(1H, dd, J=3 Hz & 13 Hz), approx. 2.3(1H, s), 2.52(1H, dd, J=11 Hz & 13 Hz), 2.87(1H, d, J=9 Hz), 3.16(3H, s), 3.20(1H, d, J=14 Hz), 3.28(3H, s), 3.40(1H, d, J=8 Hz), 3.47(1H, d, J=14 Hz), 3.96(3H, s), 4.28(1H, m), 4.73(1H, dd, J=3 Hz & 12 Hz), 5.30(1H, dd, J=9 Hz & 15 Hz), 6.04(1H, d, J=11 Hz), 6.36(1H, s), 6.42(1H, dd, J=11 Hz & 15 Hz), 6.76(s), 6.79(s), 7.1–7.5(5H, m), etc.

Mass spectrum (m/e): 622, 503, 485, 470, 468, 450,

UV spectrum ($\lambda_{max}^{MeOH}$) nm: 233.5, 252.5(sh), 281, 289.

By the same procedure as Example 1, the compounds described in the following Examples 2 to 7 were obtained. [Example No. Objective compound, (1) amount of maytansinol (mg) used, (2) corresponding isocyanate ester [amount used (mg)], (3) amount of anhydrous zinc chloride used (mg), (4) yield of the objective compound (mg), (5) m.p. of the objective compound, (6) NMR spectrum of same (δppm, 90 MHz, in CDCl$_3$, TMS), (7) UV spectrum of same ($\lambda_{max}^{MeOH}$ nm), (8) Mass spectrum (m/e) of same]

EXAMPLE 2

Maytansinol 3-(N-methyl)carbamate: (1) 100, (2) methylisocyanate(22), (3) 48, (4) 78, (5) 196°–200° C. (decompn.), (6) 0.83 (3H, s), 1.25(3H, d, J=4 Hz), 1.68(3H, s), 2.13(1H, dd, J=3 Hz & 14 Hz), 2.50(1H, dd, J=12 Hz & 14 Hz), 2.80(3H, d, J=5 Hz, s after addition of D$_2$O), 2.82(1H, d, J=9 Hz), 3.16 (3H, s), 3.20(1H, d, J=13 Hz), 3.36(3H, s), 3.47(1H, d, J=8 Hz), 3.53(1H, d, J=13 Hz), approx. 3.7(1H, broad), 3.97 (3H, s), 4.31(1H, m), 4.68(1H, dd, J=3 Hz & 12 Hz), 4.87(1H, broad quartet, J=5 Hz; disappears on addition of D$_2$O), 5.45(1H, dd, J=9 Hz & 15 Hz), 6.08(1H, d, J=10 Hz), 6.45(1H, dd, J=10 Hz & 15 Hz), 6.61(1H, s), 6.73(1H, d, J=1.5 Hz), 6.82(1H, d, J=1.5 Hz), etc. (7) 233, 243(sh), 253, 281, 289, (8) 621, 578, 560, 516, 503, 485, 470, 450.

EXAMPLE 3

Maytansinol 3-(N-butyl)carbamate: (1) 68, (2) butyl isocyanate (26), (3) 32, (4) 59, (5) 162°–165° C., (6) 0.84(3H, s), 0.94(3H, t, J=6 Hz), 1.25(3H, d, J=4 Hz), 1.2–1.7(7H, m), 1.67(3H, s), 2.14(1H, dd, J=3 Hz & 13 Hz), approx. 2.3(1H, broad), 2.44 (1H, dd, J=12 Hz & 13 Hz), 2.81(1H, d, J=9 Hz), 3.16(3H, s), 3.23(1H, d, J=12 Hz), 3.1–3.3(2H, m), 3.39(3H, s), 3.46(1H, d, J=8 Hz), 3.47(1H, d, J=12 Hz), 3.97(3H, s), 4.31(1H, m), 4.65(1H, dd, J=3 Hz & 12 Hz), 4.79(1H, broad t, J=ca 6 Hz), 5.45(1H, dd, J=10 Hz & 16 Hz), 6.04(1H, d, J=11 Hz), 6.43(1H, s), 6.44(1H, dd, J=11 Hz & 16 Hz), 6.68(1H, d, J=1.5 Hz), 6.82(1H, d, J=1.5 Hz), (7) 232.5, 243(sh), 252.5, 281, 289 (8) 663, 661, 647, 633, 620, 604, 602, 587, 574, 570, 568, 567, 560, 559, 503, 485, 470, 450, 363

EXAMPLE 4

Maytansinol 3-(N-octadecyl)carbamate: (1) 58 mg. (2) octadecyl isocyanate (140), (3) 35, (4) 58, (5) 105°–109° C., (6) 0.84 (3H, s), 0.85(3H, t, J=ca 5 Hz), 1.24(3H, d, J=4 Hz), 1.69(3H, s), 2.18(1H, dd, J=3 Hz & 14 Hz), 2.44(1H, dd, J=12 Hz & 14 Hz), 2.82(1H, d, J=9 Hz), 3.16(3H, s), 3.22(1H, d, J=13 Hz), ca 3.3(2H, m), 3.35(3H, s), 3.47(1H, d, J=8 Hz), 3.48(1H, d, J=13 Hz), ca 3.6(1H, s), 3.97(3 H, s), 4.30(1H, m), 4.67(1H, dd, J=3 Hz & 12 Hz), 4.75(1H, t, J=approx. 6 Hz, disappears on addition of D$_2$O), 5.46(1H, dd, J=9 Hz & 15 Hz), 6.05(1H, d, J=11 Hz), 6.33(1H, s), 6.45(1H, dd, J=11 Hz & 15 Hz), 6.68(1H, d, J=1.5 Hz), 6.82(1H, d, J=1.5 Hz), etc. (8) 798, 754, 723, 616, 599, 564, 503, 485, 470, 468, 450

EXAMPLE 5

Maytansinol 3-(N-cyclohexyl)carbamate, (1) 67, (2) cyclohexyl isocyanate (66), (3) 75, (4) 32, (5) 175°–178° C., (6) 0.85(3H, s), 1.27(3H, d, J=5 Hz), 1.68(3H, s), approx. 1.0–2.3(13H, m), 2.14(1H, dd, J=3 Hz & 13 Hz), 2.43(1H, dd, J=11 Hz & 13 Hz), 2.74(1H, d, J=9 Hz), 3.16(3H, s), 3.21 (1H, d, J=11 Hz), 3.36(3H, s), ca 3.4(1H, m), 3.45(1H, d, J=9 Hz), 3.47(1H, d, J=11 Hz), approx. 3.6(1H, broad), 3.96(3H, s), 4.29(1H, m), 4.63(1H, dd, J=3 Hz & 11 Hz), 4.66 (1H, t, J=7 Hz; disappears on addition of D$_2$O), 5.51(1H, dd, J=9 Hz & 15 Hz), 6.04(1H, d, J=11 Hz), 6.38(1H, s), 6.43(1H, dd, J=11 Hz & 15 Hz), 6.68(1H, d, J=1.5 Hz), 6.80(1H, d, J=1.5 Hz), etc. (7) 232.5, 243(sh), 252.5, 281, 289 (8) 628, 503, 485, 470, 450.

EXAMPLE 6

Maytansinol 3-(N-α-naphthyl)carbamate: (1) 56, (2) α-naphthyl isocyanate (185), (3) 167, (4) 17, (5) 172°–175° C., (6) 0.35(3H, s), 1.24(3H, broad), 1.65(3H, s), 2.24(1H, dd, J=3 Hz & 14 Hz), approx. 2.3(1H, broad), 2.60(1H, dd, J=10 Hz & 14 Hz), 2.96(1H, d, J=9 Hz), 3.15(1H, d, J=14 Hz), 3.20(3H, s), 3.23(3H, s), 3.35(1H, d, J=8 Hz), 3.41(1H, d, J=14 Hz), 3.97(3H, s), 4.31(1H, m), 4.82(1H, dd, J=3 Hz & 10 Hz), 5.17 (1H, dd, J=9 Hz & 15 Hz), 5.87(1H, d, J=11 Hz), 6.32(1H, s), 6.34(1H, dd, J=11 Hz & 15 Hz), 6.80(1H, d, J=1.5 Hz), 6.85(1H, d, J=1.5 Hz), 7.1–8.1(7H, m), etc. (7) 222, 252.4, 271(sh), 281, 290, (8) 672, 503, 485, 468, 450, 442, 407

EXAMPLE 7

Maytansinol 3-(N-p-ethoxyphenyl)carbamate, (1) 56.2 mg, (2) p-ethoxyphenyl isocyanate (52.3), (3) 30, (4) 50.0, (5) 221°–223° C., (6) 0.88(3H, s), 1.28(3H, d, J=6 Hz), 1.38(3H, t, J=7 Hz), 1.67 (3H, s), 2.87(1H, d, J=9 Hz), 3.18(3H, s), ca 3.19(1H, d, J=ca 15 Hz), 3.30(3H, s), 3.43(1H, d, J=9 Hz), 3.47(1H, d, J=ca 15 Hz), 3.97(3H, s), 3.98(2H, q, J=7 Hz), 4.29(1H, m), 4.74(1H, dd, J=3 Hz & 11 Hz), 5.36(1H, dd, J=9 Hz & 15 Hz), 6.05(1H, d, J=12 Hz), 6.83(2H, d, J=9 Hz), 7.32 (2H, d, J=9 Hz), etc. (7) 235–241(br.), 252(sh), 282, 288.5

EXAMPLE 8

In 10 ml of dichloromethane is dissolved 54 mg (0.0956 mmol) of maytansinol, and to the solution 50 mg (0.877 mmol) of methyl isocyanate and 30 mg of cuprous chloride are added and the mixture is stirred for 4 hours at room temperature. After filtration, the filtrate is concentrated. The residue is chromatographed on a silica gel column (25 mm in diameter×45 cm long), eluted with chloroform-methanol (40:1, V/V), and the eluate is collected in 25-gram fractions. Fractions 34 through 44 are pooled and evaporated to dryness to obtain 44 mg of white glass-like substance. This is reprecipitated from chloroform-hexane to obtain 28 mg of maytansinol 3-(N-methyl)carbamate 9-(2,4-dimethyl)allophanate as white crystal.

m.p.: 149°–151° C. (decompn.)

NMR spectrum (CDCl$_3$) δ ppm: 0.81(3H, s), 1.23(3H, d, J=ca 4 Hz), 1.65(3H, s), 2.12(1H, dd, J=3 Hz & 14 Hz), 2.35 (3H, s), 2.47(1H, dd, J=12 Hz & 14 Hz), 2.70(1H, d, J=9 Hz), 2.81(3H, d, J=5 Hz; s after addition of D$_2$O), 2.86(3H, d, J=4 Hz, s after addition of D$_2$O), 3.16(3H, s), ca 3.17(1H, d, J=ca 18 Hz), 3.26(3H, s), 3.37(1H, d, J=8 Hz), 3.47(1H, d, J=ca 18 Hz), 3.95(3H, s), 4.07(1H, m), 4.65(1H, dd, J=3 Hz & 11 Hz), ca 4.7(1H, broad), 5.49(1H, dd, J=8 Hz & 15 Hz), 5.64(1H, s), 6.04(1H, d, J=11 Hz), 6.37(1H, dd, J=11 Hz & 15 Hz), 6.70(1H, d, J=1.5 Hz), 6.80(1H, d, J=1.5 Hz), etc.

Mass spectrum (m/e): 632, 630, 616, 573, 559, 516, etc.

UV spectrum ($\lambda_{max}^{MeOH}$)nm: 232.5, 244(sh), 253.5, 281, 289.

EXAMPLE 9

As in example 8, in 1 ml of dry dichloromethane are added 5.5 mg of maytansinol, about 3.5 mg of butyl isocyanate and 3 mg of cuprous chloride. The mixture is stirred at room temperature for 5.5 hours. The reaction solution is directly chromatographed on a silica gel column (column: 20 mm in outside diameter×350 mm) and developed with chloroform-methanol (100:1, V/V), and the eluate is collected in 25-g fractions. Fractions 13 through 20 are pooled and the solvent is removed, whereby 8 mg of maytansinol 3-(N-butyl)carbamate 9-(2,4-dibutyl)allophanate as colorless glass-like substance.

Mass spectrum (m/e): 756, 700, 657, 601, 556, etc.

EXAMPLE 10

In 10 ml of dry dichloromethane is dissolved 53 mg of maytansinol. To the solution 60 μl of phenyl isocyanate and 30 mg of cuprous chloride are added and the mixture is stirred for 4.5 hours at room temperature. Thereafter, 30 μl of phenyl isocyanate and 50 mg of cuprous chloride are further added and stirred at room temperature for 2 days. By TLC (solvent: H$_2$O-saturated ethyl acetate) it is confirmed that the compound has been mostly converted to a compound Rf=ca. 0.95. Thereafter, the reaction mixture is concentrated to dryness, the residue dissolved in ethyl acetate, insolubles filtered off and the filtrate concentrated to dryness. By this procedure is obtained 96 mg of crude product. This product is chromatographed on silica gel (column: 20 mm out. dia.×400 mm) and elution is carried out with chloroform to chloroform-methanol (40:1, V/V) on a gradient basis, the eluate being collected in 25-g fractions. Fractions 52 through 60 are combined and the solvent is distilled off, whereby 28 mg of maytansinol 3-(N-phenyl)carbamate is obtained. TLC (solvent: H$_2$O—saturated ethyl acetate) R$_f$=0.65. Based on the TLC and NMR spectrum, this product was found to be identical with the compound of Example 1.

EXAMPLE 11

In 0.2 ml of dichloromethane is dissolved 10 mg of maytansinol 3-(N-methyl)carbamate 9-(2,4-dimethyl)allophanate, and two droplets of trifluoroacetic acid are added in this solution. This solution is stirred for 5 minutes at room temperature. Thereafter, dichloromethane is further added and the solution is washed with aqueous sodium hydrogen carbonate solution. The solvent is distilled off and the residue is chromatographed on silica gel (12 g) to obtain 5.2 mg of maytansinol 3-(N-methyl)carbamate.

EXAMPLE 12

In 5 ml of dry dichloromethane is dissolved 38.8 mg of dechloromaytansinol. To the solution 15 μl (ca.16.4 mg) of phenyl isocyanate and ca.20 mg of anhydrous zinc chloride are added, and the mixture is stirred at room temperature for 3 hours. The reaction solution is dilluted with dichloromethane, washed with water, and dried (Na$_2$SO$_4$), and the solvent is distilled off under reduced pressure. The residue is chromatographed on a silica gel(25 g) [solvent: ethyl acetate/H$_2$O-saturated ethyl acetate (2:1, V/V)] and the eluate is collected in 17-gram fractions. Fractions 9 through 13 are pooled, the solvent distilled off and the residue dried in vacuo to obtain 41.8 mg of dechloromaytansinol 3-(N-phenyl)-carbamate as colorless glass-like substance.

NMR spectrum (CDCl$_3$) δ ppm: 0.87(3H, s), 1.26(3H, d, J=6 Hz), 1.70(3H, s), 2.03(3H, s), 2.23(1H, dd, J=2.5 Hz & 14 Hz), 2.69(1H, dd, J=11 Hz & 14 Hz), 2.87(1H, d, J=9 Hz), 3.23(3H, s), 3.30(3H, s), 3.42(1H, d, J=9 Hz), 3.49(1H, d, J=14 Hz), 3.85(3H, s), 4.30(1H, m), 4.78(1H, dd, J=2.5 Hz & 11 Hz), 5.37(1H, dd, J=9 Hz & 15 Hz), 6.10(1H, d, J=10.5 Hz), 6.39(1H, s), 6.43(1H, dd, J=10.5 Hz & 15 Hz), 6.57-7.56(ca. 9H, m), etc.

EXAMPLE 13

In 10 ml of dichloromethane are dissolved 56.4 mg of maytansinol, 17 mg of isopropyl isocyanate and 30 mg of zinc chloride, and the mixture is stirred at room temperature overnight. The reaction mixture is washed with water and dried. The solvent is distilled off and the residue is separated and purified by chromatography on a silica gel column to obtain 30 mg of maytansinol 3-isopropylcarbamate. NMR spectrum (90 MHz, CDCl$_3$), δ 0.86(s, 3H), 1.23(d, 6H), 1.67 (s, 3H), 3.15(s, 3H), 3.35(s, 3H), 3.96(s, 3H), 5.53(dd, 1H); Mass spectrum (m/e), 588(M$^+$-61)

EXAMPLE 14

In 5 ml of dichloromethane are dissolved 95 mg of maytansinol, 202 mg of 3-pyridyl isocyanate and 42 mg of zinc chloride, and the mixture is stirred at room temperature for 5 hours. After addition of 20 ml of chloroform, the reaction mixture is washed with diluted aqueous sodium hydroxide solution and the solvent is distilled off. The residue is separated and purified by chromatography on a silica gel column to obtain 40 mg of maytansinol 3-(3-pyridyl)carbamate. NMR spectrum (90 MHz, CDCl$_3$), δ 0.88(s, 3H), 1.23(d, 3H), 1.68(s, 3H), 3.17(s, 3H), 3.28(s, 3H), 3.97(s, 3H);

Mass spectrum (m/e), 623(M$^+$-61).

EXAMPLE 15

In 2.3 ml of dichloromethane are dissolved 130 mg of maytansinol 72 mg of 5-dimethylaminopentyl isocyanate and 50 mg of zinc chloride, and the mixture is stirred at room temperature for 3 hours. The reaction solution is directly separated and purified by chromatography on a silica gel column to obtain 42 mg of maytansinol 3-(5-dimethylamino)pentylcarbamate.

Mass spectrum (m/e), 659(M+-61)

EXAMPLE 16

In 2.7 ml of dichloromethane are dissolved 153 mg of maytansinol, 70 mg of β-methoxycarbonylethyl isocyanate and 60 mg of zinc chloride, and the mixture is stirred at room temperature overnight. The reaction solution is directly separated and purified by chromatography on a silica gel column to obtain 96 mg of maytansinol 3-(β-methoxycarbonylethyl)carbamate.

NMR spectrum (90 MHz, CDCl$_3$), δ 0.83(s, 3H), 1.28(d, 3H), 1.67(s, 3H), 3.15(s, 3H), 3.35(s, 3H), 3.70(s, 3H), 3.93(s, 3H), 6.68(s, 1H), 6.82(s, 1H);

Mass spectrum (m/e), 632(M+-61).

EXAMPLE 17

In 4.0 ml of dry THF is dissolved 113 mg of maytansinol and cooled at −20° C. To this solution is added 5 molar equivalents of n-butyllithium (hexane solution) in nitrogen gas streams and under stirring, and 108 mg of N,N-dimethylcarbamoyl chloride is further added. After the mixture is stirred for 15 minutes, 1.0 ml of saturated aqueous sodium chloride solution and 20 ml of chloroform are added to it and the organic layer is separated. The solvent is distilled off under reduced pressure. The residue is purified by chromatography on a silica gel column to obtain 10 mg of maytansinol 3-N,N-dimethylcarbamate. Thin layer chromatography on silica gel (Merck HPTLC): R$_f$=0.39, (solvent: chloroform-methanol=95:5), Mass spectrum (m/e), 574 (M+-61)

EXAMPLE 18

As in Example 1, maytansinol (197 mg), p-methoxycarbonylphenylisocyanate (124 mg) and small amount of anhydrous zinc chloride are made to react in 3.5 ml of dry dichloromethane at room temperature for 5 hours. The reaction mixture is directly chromatographed on silica gel (50 g) with chloroform and then chloroform containing 2.5% of methanol as solvent to give 121 mg of maytansinol 3-(N-p-methoxycarbonylphenyl)carbamate.

NMR spectrum (CDCl$_3$-DMSO-d$_6$)δ:0.88 (3H, s), 1.20 (3H, d), 1.65 (3H, s), 3.17 (3H, s), 3.27 (3H, s), 3.85 (3H, s), 6.85 (1H, s), 7.03 (1H, s), 7.60 (2H, d), 7.92 (2H, d) etc.

Seventy four mg of this product is dissolved in 4 ml of a mixture of acetonitrile and water (2/1 (V/V)). To this, 100 μl of N NaOH is added and the solution is placed at room temperature for 1 hour. Then, each 50 μl of NaOH is further added at intervals of 30 minutes and the solution is stirred for 1 hour after the final addition of the base. Then, N HCl (200 μl) is added and the solvent is evaporated off and the residue is chromatographed on silica gel (25 g) with acetonitrile/water=85/15 (V/V) as solvent, to give 21 mg of maytansinol 3-(N-p-carboxyphenyl)carbamate as a pale yellow powder. Rf=0.25 (Merck, HPTLC; solvent, CH$_3$CN/H$_2$O=85/15 (V/V)).

EXAMPLE 19

Maytansinol 3-(N-2-methoxycarbonylethyl)carbamate (61 mg) obtained in Example 16, is dissolved in 0.5 ml of acetonitrile and 0.25 ml of water. To this, 88 μl and 44 μl of N NaOH are added at an interval of 1 hour at room temperature. The mixture is stirred for total 2 hours. Then, 132 μl of NHCl is added, followed by the evaporation of the solvent. The residue is chromatographed on silica gel (20 g) with acetonitrile containing 15% (V/V) of water as solvent, to give 44 mg of maytansinol 3-(N-2-carboxyethyl)carbamate, Rf=0.19 (Merck, HPTLC; solvent, CH$_3$CN/H$_2$O=85/15 (V/V).

EXAMPLE 20

Maytansinol 3-(N-3-pyridyl)carbamate 23 mg, obtained in Example 14 is dissolved in 0.4 ml of THF. To this, 30 mg of methyl iodide is added and the mixture is allowed to stand at room temperature overnight. Then, the solvent is evaporated off, and the residue is triturated with ether to give 30 mg of maytansinol 3-(N-3-pyridyl)carbamate N'-methiodide. Rf=0.30 (Merck, HPTLC; solvent, CH$_3$CN/H$_2$O=80/20 (V/V)).

EXAMPLE 21

In 2.0 ml of dry THF is dissolved 57 mg of maytansinol and under nitrogen gas streams and at −20° C., the solution is treated with 5 molar equivalents of 15% n-butyllithium (n-hexane solution). Then, 61 mg of isopropyl chloroformate is added and the mixture is stirred for 15 minutes. Thereafter, at 0° C., the organic layer is extracted with 0.5 ml of saturated sodium chloride and 20 ml of THF. The organic layer is dried and the solvent is distilled off. The residue is chromatographed on silica gel to obtain 5 mg of maytansinol 3-isopropylcarbonate. Thin layer chromatography on silica gel (Merck HPTLC): Rf=0.44 (developing solvent: chloroform-methanol=95:5), Mass spectrum (m/e), 650 (M+), 589 (M+-61).

EXAMPLE 22

In 6.0 ml of dry THF is dissolved 163 mg of maytansinol and under nitrogen gas streams and at −20° C., the solution is treated with 10 molar equivalents of 15% n-butyllithium (n-hexane solution). Then, 556 mg of n-octyl chloroformate is added and the mixture is stirred for 15 minutes. Thereafter, at 0° C., the organic layer is extracted with 1.0 ml of saturated sodium chloride and 20 ml of THF. The organic layer is dried, after which the solvent is distilled off. The residue is purified by silica gel chromatography to obtain 58 mg of maytansinol 3-n-octylcarbonate. Thin layer chromatography on silica gel (Merck HPTLC): Rf=0.61 (developing solvent: chloroform-methanol=95:5), Mass spectrum (m/e), 659 (M+-61).

EXAMPLE 23

In 4.4 ml of dry THF is dissolved 124 mg of maytansinol and under nitrogen gas streams and at −20° C., the solution is treated with 5 molar equivalents of 15% n-butyllithium (n-hexane solution). Then, 344 mg of phenyl chloroformate is added and the mixture is stirred for 15 minutes. Thereafter, at 0° C., the organic layer is separated after addition of 1.1 ml of saturated aqueous solution of sodium hydrogen carbonate and 33 ml of THF. The organic layer is dried, after which the solvent is distilled off. The residue is chromatographed on silica gel to recover 12 mg of maytansinol 3-phenylcarbonate. Thin layer chromatography on silica gel (Merck HPTLC): Rf=0.45 (developing solvent: chloroform-methanol=95:5), Mass spectrum (m/e), 623 (M+-61).

EXAMPLE 24

In 2.0 ml of dry THF is dissolved 53 mg of maytansinol and under nitrogen gas streams and at −20° C., the solution is treated with 10 molar equivalents of 15% n-butyllithium (n-hexane solution). Then, 10 molar equivalents of 30% benzyl chloroformate (toluene solution) is added and the mixture is stirred for 15 minutes. Therefore, at 0° C., the organic layer is separated after addition of 0.5 ml of saturated aqueous solution of sodium hydrogen carbonate and 15 ml of THF. The organic layer is dried, after which the solvent is distilled off. The residue is chromatographed on silica gel to obtain 23 mg of dechloromaytansinol 3-benzylcarbonate. Thin layer chromatography (Merck HPTLC): Rf=0.54 (developing solvent: chloroform:methanol=95:5), Mass spectrum (m/e), 603 (M+-61).

Experimental Data

Antitumor activity

Therapeutic tests were carried out in mice according to NCI-protocol 1,300, Cancer Chemother, Reports, Part 3, 1972, Vol. 3, No. 2, in which melanoma B-16 tumor cells had been intraperitoneally transplanted, compound (I) being administered intraperitoneally once daily for 9 consecutive days. Life span prolongations obtained are shown in Table 1 as T/C % values.

TABLE 1

| Compound | Dose (μg/kg) | Antitumor activities B-16 (T/C%) |
|---|---|---|
| Maytansinol | 400 | 161 |
| 3-(N-phenyl)carbamate | 200 | 151 |
|  | 100 | 123 |
| Maytansinol | 200 | 171 |
| 3-isopropylcarbonate | 100 | 171 |
|  | 50 | 150 |

Antiprotozoal activity

Antiprotozoal activity of compound (I) was assayed with *Tetrahymena pyriformis* W as the test organism and a medium composed of 20 g tryptose-peptone (Difco Co.), 1 g yeast extract, 2 g glucose, 1000 ml distilled water, 10 ml 1 M phosphate buffer (pH 7.0) as the assay medium. The microorganism was incubated at 28° C. for 44 to 48 hours and the growth inhibitory activity of compound (I) was assayed by the serial dilution method. The minimal inhibitory concentrations of compound (I) are shown in Table 2.

TABLE 2

| Compound | Antiprotozoal activity MIC (μg/ml) *Tetrahymena pyriformis* W |
|---|---|
| Maytansinol 3-(N-phenyl)carbamate | ≧8 |
| Maytansinol 3-isopropylcarbonate | 4-8 |

EXAMPLES OF PHARMACEUTICAL COMPOSITIONS

Example A

| Composition for Injection | |
|---|---|
| (1) Maytansinol 3-isopropylcarbonate | 100 mg |
| (2) Ethanol | 10 g |
| (3) Polysorbate 80 (Tween 80) | 40 g |
| (4) Mannitol | 20 g |
| (5) Distilled water, a sufficient quantity to make | 1000 ml |

Preparation (1) is dissolved in (2). To this solution, (3) and (4) are added, followed by the addition of sterilized distilled water to make 1000 ml of the solution. Ten milliliter each of the solution is used to fill 100 amber ampoules and the air within the ampoules is replaced with nitrogen gas, then the ampoule is sealed. All the processes are conducted under sterile conditions.

EXAMPLE B

| Composition for Injection | |
|---|---|
| (1) Maytansinol 3-(N-phenyl)carbamate | 200 mg |
| (2) Ethanol | 5 g |
| (3) Polysorbate 80 (Tween 80) | 100 g |
| (4) Mannitol | 20 g |
| (5) Distilled water, a sufficient quantity to make | 1000 ml |

Preparation

By a similar procedure to that of Example A, an injectable solution of (1) is prepared.

What is claimed is:

1. A compound of the formula:

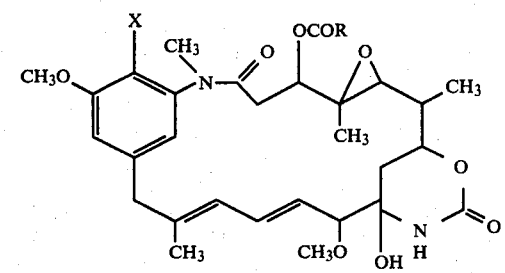

wherein X is H or Cl, and R is

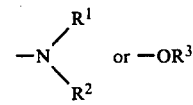

wherein $R^1$ and $R^2$ may be the same or different, and each is H or a hydrocarbon residue of the class consisting of $C_{1-18}$ alkyl, $R_{1-18}$ alkenyl, $C_{3-10}$ cycloalkyl to which a benzene ring may be fused, $C_{3-10}$ cycloalkenyl, $C_{3-10}$ cycloalkyl-$C_{1-6}$ alkyl, $C_{3-10}$ cycloalkenyl-$C_{1-6}$alkyl, phenyl, naphthyl, phenyl-$C_{1-6}$ alkyl, phenyl-$C_{3-10}$ cycloalkyl, $C_{3-10}$cycloalkylphenyl, biphenyl, or a heterocyclic group of the class consisting of azetidinyl, pyrrolyl, furyl, thienyl, thiazolyl, isothiazolyl, oxazolyl, isoxazolyl, pyrazolyl, imidazolyl, pyridyl, pyrimidinyl, pyrazinyl, triazinyl, quinolyl, quinazolyl, quinoxalyl, indolyl, benzofuranyl, and benzothienyl, said hydrocarbon residue or heterocyclic group being unsubstituted or substituted by $C_{1-4}$ alkyl, $C_{1-4}$ alkoxy, $C_{1-4}$ alkylthio, phenoxy, phenythio, cyclohexyloxy, halogen, cyano, carboxyl, $C_{2-5}$ alkoxycarbonyl, benzyloxycarbonyl, nitro, aminosulfonyl or di-$C_{1-4}$ alkylamino; or $R^1$ and $R^2$ may, taken together with the adjacent N atom, form an azetidinyl, pyrrolinyl, piperazinyl, or morpholinyl group, and wherein $R^3$ is a hydrocarbon residue of the class consisting of $C_{1-18}$ alkyl, $C_{3-10}$ cycloalkyl, phenyl, naphthyl or phenyl-$C_{1-4}$ alkyl, said hydrocarbon residue being unsubstituted or substituted by $C_{1-4}$ alkyl, halogenated $C_{1-4}$ alkyl, $C_{1-4}$ alkoxy, phenoxy, benzyloxy, halogen or cyano.

2. A compound according to claim 1, wherein R is

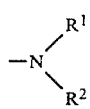

wherein $R^1$ and $R^2$ may be the same or different, and each is H or a hydrocarbon residue of the class consisting of $C_{1-18}$ alkyl, $C_{1-18}$ alkenyl, $C_{3-10}$ cycloalkyl to which a benzene ring may be fused, $C_{3-10}$ cycloalkenyl, $C_{3-10}$ cycloalkyl-$C_{1-6}$ alkyl, $C_{3-10}$ cycloalkenyl-$C_{1-6}$ alkyl, phenyl, naphthyl, phenyl-$C_{1-6}$ alkyl, phenyl-$C_{3-10}$ cycloalkyl, $C_{3-10}$ cycloalkylphenyl, biphenyl, or a heterocyclic group of the class consisting of azetidinyl, pyrrolyl, furyl, thienyl, thiazolyl, isothiazolyl, oxazolyl, isoxazolyl, pyrazolyl, imidazolyl, pyridyl, pyrimidinyl, pyrazinyl, triazinyl, quinolyl, quinazolyl, quinoxalyl, indolyl, benzofuranyl, and benzothienyl, said hydrocarbon residue or heterocyclic group being unsubstituted or substituted by $C_{1-4}$ alkyl, $C_{1-4}$ alkoxy, $C_{1-4}$ alkylthio, phenoxy, phenylthio, cyclohexyloxy, halogen, cyano, carboxyl, $C_{2-5}$ alkoxycarbonyl, benzyloxycarbonyl, nitro, aminosulfonyl or di-$C_{1-4}$ alkylamino; or $R^1$ and $R^2$ may, taken together with the adjacent N atom, form an azetidinyl, pyrrolidinyl, piperazinyl or morpholinyl group.

3. A compound according to claim 2, wherein $R^1$ and $R^2$ may be the same or different, and each is H, $C_{1-18}$ alkyl, $C_{3-7}$ cycloalkyl, phenyl, naphthyl or pyridyl, said alkyl, cycloalkyl, phenyl, naphthyl and pyridyl being unsubstituted or substituted by $C_{1-4}$ alkyl, $C_{1-4}$ alkoxy, carboxyl, $C_{2-5}$ alkoxycarbonyl or di-$C_{1-4}$ alkylamino.

4. A compound according to claim 1, wherein R is -$OR^3$ wherein $R^3$ is $C_{1-18}$ alkyl, $C_{3-10}$ cycloalkyl, phenyl, naphthyl or phenyl-$C_{1-4}$ alkyl, said hydrocarbon residues being unsubstituted or substituted by $C_{1-4}$ alkyl, halogenated $C_{1-4}$ alkyl, $C_{1-4}$ alkoxy, phenoxy, benzyloxy, halogen or cyano.

5. A compound according to claim 4, wherein $R^3$ is $C_{1-8}$ alkyl, phenyl or phenyl-$C_{1-4}$ alkyl.

6. The compound according to claim 1, which is maytansinol 3-N-phenylcarbamate.

7. The compound according to claim 1, which is maytansinol 3-isopropylcarbonate.

8. A pharmaceutical composition suitable for inhibiting the growth of tumour cells and prolonging the survival time of a tomour-bearing warm-blooded animal, which comprises as an active ingredient an effective amount of a compound of the following formula (I) and a pharmaceutically acceptable carrier or diluent therefor:

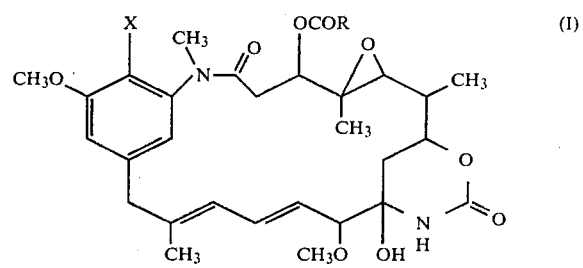

wherein X is H or Cl, and R is

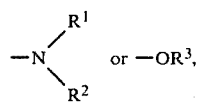

wherein $R^1$ and $R^2$ may be the same or different, and each is H is a hydrocarbon residue of the class consisting of $C_{1-18}$ alkyl, $C_{1-18}$ alkenyl, $C_{3-10}$ cycloalkyl to which a benzene ring may be fused, $C_{3-10}$ cycloalkenyl, $C_{3-10}$ cycloalkyl-$C_{1-6}$ alkyl, $C_{3-10}$ cycloalkenyl-$C_{1-6}$ alkyl, phenyl, naphthyl, phenyl-$C_{1-6}$ alkyl, phenyl-$C_{3-10}$ cycloalkyl, $C_{3-10}$ cycloalkylphenyl, biphenyl, or a heterocyclic group of the class consisting of azetidinyl, pyrrolyl, furyl, thienyl, thiazolyl, isothiazolyl, oxazolyl, isoxazolyl, pyrazolyl, imidazolyl, pyridyl, pyrimidinyl, pyrazinyl, triazinyl, quinolyl, quinazolyl, quinoxalyl, indolyl, benzofuranyl, and benzothienyl, said hydrocarbon residue or heterocyclic group being unsubstituted or substituted by $C_{1-4}$ alkyl, $C_{1-4}$ alkoxy, $C_{1-4}$ alkylthio, phenoxy, phenylthio, cyclohexyloxy, halogen, cyano, carboxyl, $C_{2-5}$ alkoxycarbonyl, benzyloxycarbonyl, nitro, aminosulfonyl or di-$C_{1-4}$ alkylamino; or $R^1$ and $R^2$ may, taken together with the adjacent N atom, form an azetidinyl, pyrrolidinyl, piperazinyl or morpholinyl group, and wherein $R^3$ is a hydrocarbon residue of the class consisting of $C_{1-18}$ alkyl, $C_{3-10}$ cycloalkyl, phenyl, naphthyl or phenyl-$C_{1-4}$ alkyl, said hydrocarbon residue being unsubstituted or substituted by $C_{1-4}$ alkyl, halogenated $C_{1-4}$ alkyl, $C_{1-4}$ alkoxy, phenoxy, benzyloxy, halogen or cyano.

9. A method for inhibiting the growth of tumour cells and prolonging the survival time of a tumour-bearing warm-blooded animal, which comprises administering to said animal an effective amount of a compund of the formula:

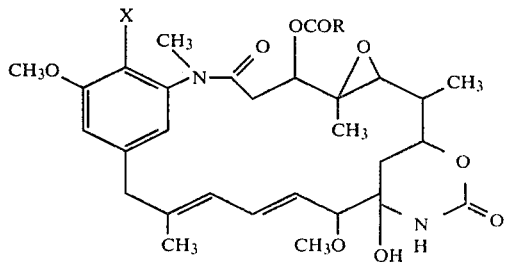

wherein X is H or Cl, and R is

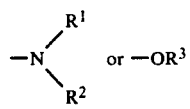

wherein $R^1$ and $R^2$ may be the same or different, and each is H or a hydrocarbon residue of the class consisting of $C_{1-18}$ alkyl, $C_{1-18}$ alkenyl, $C_{3-10}$ cycloalkyl to which a benzene ring may be fused, $C_{3-10}$ cycloalkenyl, $C_{3-10}$ cycloalkyl-$C_{1-6}$ alkyl, $C_{3-10}$ cycloalkenyl-$C_{1-6}$ alkyl, phenyl, naphthyl, phenyl-$C_{1-6}$ alkyl, phenyl-$C_{3-10}$ cycloalkyl, $C_{3-10}$ cycloalkylphenyl, biphenyl, or a heterocyclic group of the class consisting of azetidinyl, pyrrolyl, furyl, thienyl, thiazolyl, isothiazolyl, oxazolyl, isoxazolyl, pyrazolyl, imidazolyl, pyridyl, pyrimidinyl, pyrazinyl, triazinyl, quinolyl, quinazolyl, quinoxalyl, indolyl, benzofuranyl, and benzothienyl, said hydrocarbon residue or heterocyclic group being unsubstituted or substituted by $C_{1-4}$ alkyl, $C_{1-4}$ alkoxy, $C_{1-4}$ alkylthio, phenoxy, phenylthio, cyclohexyloxy, halogen, cyano, carboxyl, $C_{2-5}$ alkoxycarbonyl, benzyloxycarbonyl, nitro, aminosulfonyl or di-$C_{1-4}$ alkylamino; or $R^1$ and $R^2$ may, taken together with the adjacent N atom, form an acetidinyl, pyrrolidinyl, piperazinyl or morpholinyl group, and wherein $R^3$ is a hydrocarbon residue of the class consisting of $C_{1-18}$ alkyl, $C_{3-10}$ cycloalkyl, phenyl, naphthyl or phenyl-$C_{1-4}$ alkyl, said hydrocarbon residue being unsubstituted or substituted by $C_{1-4}$ alkyl, halogenated $C_{1-4}$ alkyl, $C_{1-4}$ alkoxy, phenoxy, benzyloxy, halogen or cyano.

* * * * *